US006126754A

United States Patent [19]

Duflot

[11] Patent Number: 6,126,754

[45] Date of Patent: Oct. 3, 2000

[54] PROCESS FOR THE MANUFACTURE OF A STARCH HYDROLYSATE WITH HIGH DEXTROSE CONTENT

[75] Inventor: Pierrick Duflot, Lacouture, France

[73] Assignee: Roquette Freres, Lestrem, France

[21] Appl. No.: 09/328,520

[22] Filed: Jun. 9, 1999

[30] Foreign Application Priority Data

Apr. 2, 1999 [FR] France .................................. 99 04177

[51] Int. Cl.$^{7}$ .......................... C13K 13/00; C12P 19/20; C12P 19/14

[52] U.S. Cl. ................................ 127/55; 127/40; 435/96; 435/98; 435/99

[58] Field of Search .......................... 127/40, 55; 435/96, 435/98, 99

[56] References Cited

U.S. PATENT DOCUMENTS

| | | |
|---|---|---|
| 4,422,881 | 12/1983 | Devos et al. . |
| 4,594,322 | 6/1986 | Thompson et al. . |
| 5,869,297 | 2/1999 | Binder et al. . |

FOREIGN PATENT DOCUMENTS

| | | |
|---|---|---|
| 0 452 238 | 10/1991 | European Pat. Off. . |
| WO 99/27124 | 6/1999 | WIPO . |

OTHER PUBLICATIONS

Abstract of FR 2 762 616 (at 1998).
WPIL Abstract in English of FR 2 762 616 (Oct. 1998).

*Primary Examiner*—David Brunsman
*Attorney, Agent, or Firm*—Henderson & Sturm LLP

[57] ABSTRACT

The invention concerns a process for the manufacture of a starch hydrolysate with high dextrose content comprising the stages of:

(a) liquefying starch milk with the aid of an α-amylase so as to obtain a liquefied starch milk;

(b) saccharifying the liquefied starch milk, with the aid of a glucogenic enzyme, to obtain a raw saccharified hydrolysate;

(c) separating the raw saccharified hydrolysate by nanofiltration over membranes so as to collect a nanofiltration permeate constituting said starch hydrolysate with high dextrose content and a nanofiltration retentate.

9 Claims, No Drawings

PROCESS FOR THE MANUFACTURE OF A STARCH HYDROLYSATE WITH HIGH DEXTROSE CONTENT

FIELD OF THE INVENTION

The invention relates to a process for the manufacture of a starch hydrolysate with high dextrose content.

It also relates to a process for the manufacture of sorbitol from a starch hydrolysate with high dextrose content manufactured by the process in accordance with the invention.

BACKGROUND OF THE INVENTION

It is known how to manufacture starch hydrolysates for which the dextrose equivalent value (the reductive power expressed in glucose over dry matter, henceforth DE) is in the range 2 to 98 and which, depending on this value, can contain up to 96% of actual dextrose. These different qualities of starch hydrolysates are obtained by selecting the conditions of the hydrolysis of the starch. The nature of the hydrolysis, that is, whether it is acid or enzymatic, also plays a part.

Starch hydrolysates rich in dextrose, although they have numerous spheres of application, are primarily used as a raw material in the manufacture of crystallised dextrose or as a substrate for the manufacture of fructose by isomerisation. For these two applications, the highest possible conversion is sought, that is, the highest possible extrose content, with a minimum of impurities.

The starch conversion processes using an acid give starch hydrolysates in which the dextrose content does not exceed 85% to 90%. These processes in fact favour the concurrent reactions of reversion and internal dehydration of the dextrose.

The starch conversion processes using both an acid and an enzyme (usually a glucoamylase) give starch hydrolysates in which the dextrose content is never above 93%. In fact, in such processes, the acid hydrolysis of the starch produces highly branched saccharides which resist the action of the glucoamylase.

The starch hydrolysates obtained by double enzymatic conversion with α-amylase and with amyloglucosidase (or glucoamylase), usually titrate from 93% to 95% of actual dextrose, and contain in the range from 5% to 7% of residual oligosaccharides and polysaccharides, the majority of which consists of disaccharides (maltose and isomaltose).

These hydrolysates are obtained in the usual way by liquefaction of the starch up to a DE in the range from 12 to 20, followed by saccharification with amyloglucosidase, but in these conditions the actual dextrose content cannot exceed 94% to 95%.

In order to obtain higher actual dextrose contents, several processes have been proposed to either improve the conversion of the starch by limiting the formation of co-products or to improve the efficacy of the separation dextrose/co-products (oligosaccharides and polysaccharides).

Thus a first process consists in carrying out the stages of liquefaction and saccharification at very low dry matter contents (in the order of 5% to 10%). But even at such low dry matter levels, the actual dextrose content does not exceed 95% to 97%. In addition, such a process is not at all economically viable because of the energy required for evaporation of the water.

Another process consists in carrying out the saccharification in the presence of an enzyme which hydrolyses the 1–6 bonds of the starch, but even in this case, the dextrose content is only 96% to 97% maximum.

Yet another process consists in separating, by a method known per se, the dextrose and the oligosaccharides and polysaccharides by passing the hydrolysate over a column of a molecular sieve such as a cationic resin. In such a process, the aqueous starch hydrolysate having previously undergone a pre-treatment such as concentration, filtration and/or bleaching, is adsorbed over the column, and the co-products (the polysaccharides and some of the oligosaccharides) end up in the raffinate excluded from the sieve. The dextrose is then desorbed by elution with water, and the water is then partially or completely eliminated to form a concentrated dextrose solution or crystallised dextrose.

Another process, based on the same principle as the one above, consists in separating the dextrose and the oligosaccharides and polysaccharides by passing the starch hydrolysate over tangential filtration membranes. Such a process is described in documents FR-A-2.762.616 and U.S. Pat. No. 5,869,297.

This last process effectively permits the obtention of a starch hydrolysate with a high actual dextrose content of more than 98%-99%, but the yields obtained are unfortunately too low (in the order of 20% to 25%) to justify such processes from the industrial and economic points of view.

OBJECTS AND SUMMARY OF THE INVENTION

A first object of the present invention is therefore to propose a process for the manufacture of a starch hydrolysate with a high dextrose content which overcomes the limits and/or disadvantages of the prior art processes.

Another object of the present invention is to propose a process for the manufacture of a starch hydrolysate with a high dextrose content, over 97% and, even more preferably, over 99%.

Another object of the present invention is to propose such a process, simple and economically-competitive, which allows the obtention of hydrolysates with such high level of actual dextrose content with extremely satisfactory yields.

To this end, the invention proposes a process for the manufacture of a starch hydrolysate with high dextrose content which includes the following stages:

(a) liquefying a starch milk with the aid of an α-amylase so as to obtain a liquefied starch milk;

(b) saccharifying the liquefied starch milk, with the aid of a glucogenic enzyme, to obtain a raw saccharified hydrolysate;

(c) separating the raw saccharified hydrolysate by nanofiltration over membranes so as to collect a nanofiltration permeate constituting said starch hydrolysate with high dextrose content and a nanofiltration retentate.

Following detailed research, the applicants ascertained that in a process for the manufacture of a starch hydrolysate with high dextrose content implementing a stage of membrane separation, the dextrose content of the permeate is better if the saccharified starch hydrolysate to be separated is kept in its raw form.

In the context of the present invention, raw saccharified starch hydrolysate means a starch hydrolysate which has been stripped of its insoluble matter and which has not undergone any purification treatment designed to eliminate the soluble matter (enzymes, proteins, amino acids, colorants, salts,.).

Thus, as opposed to the teaching of the prior art which usually includes a stage of inhibition of the saccharification enzyme (to avoid the formation of reversion products) at the end of the saccharification, in the present invention we are seeking, on the contrary, to maintain a saccharifying enzymatic activity within the saccharified starch hydrolysate.

We are also seeking, in the present invention, to maintain the presence of charges within the saccharified starch hydrolysate. In the conventional prior art processes, these charges are usually eliminated by passing the saccharified starch hydrolysate over carbon black and over a demineralisation resin. In the present invention, the hydrolysate is not demineralised.

The first stage of the process according to the present invention therefore consists in liquefying a starch milk with the aid of an α-amylase.

It is preferred, advantageously in the process according to the invention, to carry out a graded hydrolysis of the starch milk so as to produce a liquefied starch milk with a low transformation rate.

Thus, in the process according to the invention, stage (a) of liquefaction is carried out preferably to a DE in the range from 2 to 10, and more particularly to a DE in the range from 4 to 8.

Liquefying the starch milk at an extremely low DE in the range from 2 to 10 (and preferably from 4 to 8), in combination with inhibiting the liquefying enzyme at the end of liquefaction, favours the obtention of a final hydrolysate which exhibits the sought characteristics, i.e. which has a high dextrose content and a specific non-dextrose content which is basically the result of the presence of polysaccharides and not of di- or oligosaccharides.

Preferably, the liquefaction stage is carried out in two sub-stages, the first consisting in heating the starch milk, for a few minutes and at a temperature in the range 105° C. to 108° C., together with the enzyme (of the type THERMAMYL 120L, marketed by the NOVO Company) and an activator based on calcium, and the second consisting in heating the starch milk thus treated to a temperature in the range 95° C. to 100° C. for one to two hours.

When the liquefaction stage has been completed, under conditions of dry matter contents, pH, enzyme level and calcium level well known to the skilled person, and after advantageously inhibiting the liquefying enzyme (for example, on exit from liquefaction, a thermal shock of a few seconds at a temperature above or equal to 130° C.), stage (b) of saccharification of the liquefied starch milk is performed.

During this stage, the liquefied starch milk is subjected to the action of a glucogenic enzyme, in particular selected from the group consisting of amyloglucosidase, glucoamylase or any other glucogenic enzyme.

To avoid reversion reactions and the formation in particular of disaccharides (maltose, isomaltose) by repolymerisation of dextrose, the saccharification stage is carried out under known conditions and in a known manner, over 24 hours at most.

In fact, the preferred substrate of glucogenic enzymes is of a high molecular weight, and the α-1,4 bonds of starch are hydrolysed much more rapidly than the α-1,6 bonds. Consequently, at the beginning of the saccharification, as the large molecules and the α-1,4 bonds predominate, the production of dextrose is extremely rapid, while the production of reversion products is very slow, due to the low dextrose concentration of the reaction medium.

As saccharification continues and the small molecules and the α-1,6 bonds become predominant, the level of dextrose production progressively falls while the production of the reversion products (highly branched oligosaccharides) accelerates.

To remedy this phenomenon, it may be useful to combine an enzyme which specifically hydrolyses the α-1,6 bonds of the starch with the glucogenic enzyme. This addition of a disbranching enzyme, on the one hand, accelerates hydrolysis reactions without simultaneously accelerating reversion reactions and, on the other, reduces the quantity of highly branched oligosaccharides normally resistant to the action of the glucogenic enzyme. The disbranching enzyme is preferably isoamylase or pullulanase.

The quantities and conditions of action of the different enzymes used in the process according to the invention are chosen from among the following:

α-amylase: 20 to 2,000 KNU (Kilo Novo Units) per kilogram of dry substrate, temperature in the range 80° C. to 150° C., duration of action in the range 2 to 15 minutes.

amyloglucosidase: 4,000 to 400,000 international units per kilogram of dry substrate, temperature in the range 50° C. to 60° C., duration of action 24 hours maximum, pH in the range 4 to 6.

pullulanase: 150 to 15,000 ABM units.

The enzymes used may be of bacterial or fungal origin.

The hydrolysate thus saccharified is then advantageously filtered, preferably by microfiltration over membranes. The conditions for this treatment, particularly with regard to temperature, are selected so as to maintain a saccharifying enzymatic activity within the saccharified starch hydrolysate. This is why, in a preferred embodiment of the invention, the raw saccharified hydrolysate is microfiltered at a temperature lower than or equal to the inhibition temperature of the glucogenic enzyme (the saccharification enzyme) and advantageously at a temperature substantially equivalent to the saccharification temperature. Thus, if the saccharification temperature is in the range 50° C. to 60° C., the microfiltration should be carried out at a temperature in the range 50° C. to 60° C.

The microfiltration membrane used in the process according to the invention advantageously has a porosity in the range 50 nm to 200 nm, this porosity preferably being in the order of 50 nm. The operating temperature is in the range 50° C. to 60° C. and the pressure (transmembranal) is in the range 1 to 2 bars. A microfiltration membrane advantageously used in the process according to the invention is that marketed by the SCT Company (4 mm diameter channels).

The raw saccharified hydrolysate, which may be microfiltered but not demineralised, is then separated by nanofiltration over membranes so as to collect a nanofiltration permeate constituting the starch hydrolysate with high dextrose content and a nanofiltration retentate.

Contrary to all expectations, the applicants in fact observed, under the same operating conditions, an improved dextrose enrichment of the permeate when the saccharified hydrolysate to be nanofiltered was not demineralised. Without wishing to be restricted by a theory, the applicants considers that this improved enrichment is due to the formation of a larger polarisation layer on the surface of the membrane, the formation of this supplementary filtration layer allowing for the obtention of a higher dextrose content in the permeate.

According to a preferred embodiment, separation over membranes is performed under temperature conditions in the range 30° C. to 60° C., preferably in the range 40° C. to 50° C., and under pressure conditions in the range 15 to 35 bars, preferably in the range 20 to 30 bars. The nanofiltration membrane advantageously used in the process according to the invention is of the type NF40 marketed by the FILMTEC Company or of the type DESAL 5 DL 3840 marketed by the DESALINATION SYSTEMS Company.

In a particular embodiment of the process according to the invention, a saccharification of at least a part of the nanofiltration retentate is carried out so as to obtain a saccharified nanofiltration retentate. This secondary saccharification is possible because throughout the whole process according to the invention, everything necessary has been done to maintain a saccharifying enzyme activity within the hydrolysate, in particular at the saccharification stage by not inhibiting the glucogenic enzyme at the end of the hydrolysis and at the nanofiltration stage by working under temperature conditions similar to those of the saccharification stage.

This saccharified nanofiltration retentate, which may have a dextrose content of up to 90%, is then subjected to molecular sieving so as to collect a fraction with higher dextrose content and a fraction with lower dextrose content.

This molecular sieving stage may consist, for example, in a chromatographic separation stage or a separation over membranes stage.

The chromatographic fractionation stage is carried out by a method known per se, either discontinuously or continuously (simulated mobile bed), over adsorbents of the cationic resin type, or over strongly acid zeolites, preferably charged with alkaline or alkaline-earth ions such as calcium or magnesium ions but more preferably with sodium ions.

According to a preferred embodiment, the chromatographic fractionation is carried out using the process and equipment described in U.S. patent U.S. Pat. No. 4,422,881, owned by the Assignee. Whatever the chromatographic process adopted, the adsorbent to be preferred is a strong cationic resin used in sodium or potassium form and crosslinked with approximately 4 to 10% divinylbenzene. Resins are advantageously homogeneous in particule size and in the range of 100 to 800 micrometers.

The choice of the chromatographic fractionation parameters, among which in particular the elution rate, the starting hydrolysate feed rate, the extraction rate of the fraction-containing the starch hydrolysate with high dextrose content, the rate of the fraction containing the high molecular weight impurities and the composition of the areas of desorption, adsorption and enrichment, is made in such a way that the first dextrose-enriched fraction, with a dextrose content above 99%, is recovered with the highest possible yield.

To reach this result, these parameters are selected as follows when chromatographic fractionation is carried out, using the process and equipment described in U.S. Pat. No. 4,422,881 and when the adsorbent used is a cationic resin of low particle size cross-linked to 8% divinylbenzene and used in sodium form:

elution rate in the range 70 to 700 $l/h/m^3$ of adsorbent, starting hydrolysate feed rate in the range 10 to 100 $l/h/m^3$ of adsorbent, extraction rate of the dextrose-enriched fraction in the range 80 to 800 $l/h/m^3$, rate of the fraction enriched in oligo- and polysaccharides in the range 20 to 200 $l/h/m^3$ of adsorbent.

Instead of the chromatographic separation stage, it is possible, in the process according to the invention, to implement a stage of separation by nanofiltration over membranes, of the type described above.

The dextrose-enriched fraction obtained at the end of the chromatography or nanofiltration stage may then be mixed with the starch hydrolysate with high dextrose content obtained previously.

According to a preferred embodiment of the invention, the process which has just been described is continuous.

This hydrolysate (as well as the fraction with a lower dextrose content) obtained in accordance with the process of the invention may then be easily catalytically hydrogenised.

The hydrogenation of such a hydrolysate is carried out in accordance with the rules of the art which are used for example in the production of sorbitol from glucose.

For this stage ruthenium based catalysts and Raney nickel catalysts serve equally well. However, Raney nickel catalysts are preferred, as they are less expensive.

In practice, a catalyst in the range 1% to 10% by weight in proportion to the dry matter of the hydrolysate subjected to hydrogenation is used. Hydrogenation is preferably carried out on a hydrolysate in which the dry matter is in the range of 15% to 50%, in practice around 30% to 45%, under hydrogen pressure in the range 20 to 200 bars. It may be carried out continuously or discontinously.

When it is performed discontinously, the hydrogen pressure used is usually in the range 30 to 60 bars and the temperature at which hydrogenation takes place is in the range 100° C. to 150° C. It is also necessary to ensure that the pH of the hydrogenation medium is maintained by the addition of soda or carbonate of soda, for example, but without exceeding a pH of 9.0. This avoids the appearance of cracking or isomerisation products.

The reaction is stopped when the sugar content of the reaction medium has fallen below 1%, preferably below 0.5% and even more particularly below 0.1%.

After cooling of the reaction medium, the catalyst is eliminated by filtration and the sorbitol thus obtained is demineralised over cationic and anionic resins. At this stage, the syrups contain at least 98% of sorbitol and it is easy to purify this by crystallisation after concentration and cooling of the solutions.

MORE DETAILED DESCRIPTION

Other features and advantages of the invention will emerge on reading the following examples. They are given to illustrate the invention and are non-limiting.

EXAMPLE 1

A starch milk is liquefied in the usual way using 0.5 per thousand of THERMAMYL 120L (α-amylase marketed by the NOVO Company) to a DE of 6.5.

The reaction medium is then heated for a few seconds at 140° C. so as to inhibit the α-amylase.

The 35% dry matter hydrolysate is then saccharified by a method known per se with 0.8 per thousand of amyloglucosidase G990 marketed by the ABM Company (temperature: 60° C., pH =4.5).

After 24 hours of saccharification, a hydrolysate is obtained which has the following glucidic spectrum:

glucose: 93%

DP2: 2.5%

DP3: 0.5%

Higher DPs: 4% the abbreviation "DP" meaning degree of polymerisation.

The enzyme activity measured is 3 U/l.

The hydrolysate thus saccharified is then filtered by microfiltration over membranes.

The operating conditions are as follows:

SCT membrane: 50 nm

Temperature: 60° C.

Pressure: 2 bars

The enzyme activity measured is 2.5 U/l.

The hydrolysate thus microfiltered is separated into two to give hydrolysate A and hydrolysate B.

According to the present invention, hydrolysate A is not demineralised. Hydrolysate B is however demineralised by passage over carbon black and resin.

Each of the hydrolysates A and B is subjected to nanofiltration under the following operating conditions:

DESAL 5 DL membrane

Temperature: 45° C.

Pressure: 25 bars

The features of the permeates and retentates of nanofiltration A and B of hydrolysates A and B are as follows:

| | Dextrose/purity | Enzyme activity |
|---|---|---|
| Permeate A | 99.7% | 0 U/l |
| Retentate A | 80% | 7 U/l |
| Permeate B | 98.5% | 0 U/l |
| Retentate B | 80% | 0 U/l |

EXAMPLE 2

The retentate A according to the invention obtained in example 1 is adjusted to a dry matter of 30% and brought to 60° C. and pH 4.5. Under the action of the concentrated enzyme activity of amyloglucosidase, the dextrose content of this retentate changes from 80% to 90% over 24 hours of saccharification.

EXAMPLE 3

Permeate A of example 1, purified then concentrated to a dry matter of 45%, is subjected to catalytic hydrogenation in the presence of 5% by weight in proportion to the dry matter of Raney nickel.

The operating conditions are as follows:

temperature: 140° C.

pressure: 60 bars duration: 2 hours

Hydrogenation is stopped when the reducing sugar content of the reaction medium is lower than 600 ppm.

After cooling of the reaction medium, the catalyst is eliminated by filtration, the syrup obtained is then demineralised and finally it is concentrated to 70% of dry matter.

The composition on dry of the syrup thus obtained is as follows:

sorbitol: 98.6% mannitol: 0.4% iditol and cracking products: 0.2%

What is claimed is:

1. A process for the manufacture of a starch hydrolysate with high dextrose content, comprising the stages of:

(a) liquefying a starch milk with the aid of an α-amylase so as to obtain a liquefied starch milk;

(b) saccharifying the liquefied starch milk, with the aid of a glucogenic enzyme, to obtain a raw saccharified hydrolysate (c) separating the raw saccharified hydrolysate by nanofiltration over membranes so as to collect a nanofiltration permeate constituting said starch hydrolysate with high dextrose content and a nanofiltration retentate.

2. A process according to claim 1, wherein stage (b) of saccharification is carried out for a maximum of 24 hours.

3. A process according to claim 1, wherein the raw saccharified hydrolysate is microfiltered.

4. A process according to claim 3, wherein the microfiltration is carried out at a temperature lower than or equal to the inhibition temperature of the glucogenic enzyme.

5. A process according to claim 4, wherein the microfiltration is carried out at a temperature substantially equivalent to the saccharification temperature.

6. A process according to claim 1, wherein at least part of the nanofiltration retentate is saccharified so as to obtain a saccharified nanofiltration retentate.

7. A process according to claim 6, wherein said saccharified nanofiltration retentate is molecular sieved in order to collect a fraction with a higher dextrose content and a fraction with a lower dextrose content.

8. A process according to claim 7, wherein said fraction with a higher dextrose content is mixed with said starch hydrolysate with high dextrose content.

9. A process for the manufacture of sorbitol by hydrogenation of a starch hydrolysate with high dextrose content, wherein said hydrolysate is obtained by the process according to claim 1.

* * * * *